(12) United States Patent
Rowland

(10) Patent No.: US 10,808,197 B2
(45) Date of Patent: Oct. 20, 2020

(54) ALKYLATED ALKOXYDIARYLAMINE ANTIOXIDANTS

(71) Applicant: LANXESS Solutions US Inc., Middlebury, CT (US)

(72) Inventor: Robert G. Rowland, Woodbridge, CT (US)

(73) Assignee: LANXESS Solutions US Inc., Shelton, CT (US)

( * ) Notice: Subject to any disclaimer, the term of this patent is extended or adjusted under 35 U.S.C. 154(b) by 14 days.

(21) Appl. No.: 15/703,388

(22) Filed: Sep. 13, 2017

(65) Prior Publication Data

US 2018/0079984 A1     Mar. 22, 2018

Related U.S. Application Data

(60) Provisional application No. 62/396,885, filed on Sep. 20, 2016, provisional application No. 62/463,834, filed on Feb. 27, 2017.

(51) Int. Cl.

| | | |
|---|---|---|
| *C10M 133/14* | (2006.01) | |
| *C07C 217/92* | (2006.01) | |
| *C10M 105/00* | (2006.01) | |
| *C10M 133/12* | (2006.01) | |
| *C10M 169/04* | (2006.01) | |
| *C10N 30/04* | (2006.01) | |
| *C10N 30/10* | (2006.01) | |
| *C10M 133/54* | (2006.01) | |
| *C10N 40/04* | (2006.01) | |
| *C10N 40/08* | (2006.01) | |
| *C10N 40/20* | (2006.01) | |
| *C10N 40/25* | (2006.01) | |

(52) U.S. Cl.
CPC ......... *C10M 133/54* (2013.01); *C07C 217/92* (2013.01); *C10M 105/00* (2013.01); *C10M 133/12* (2013.01); *C10M 133/14* (2013.01); *C10M 169/04* (2013.01); *C10M 2203/003* (2013.01); *C10M 2215/062* (2013.01); *C10M 2215/064* (2013.01); *C10M 2215/065* (2013.01); *C10M 2215/26* (2013.01); *C10N 2030/04* (2013.01); *C10N 2030/10* (2013.01); *C10N 2040/04* (2013.01); *C10N 2040/08* (2013.01); *C10N 2040/20* (2013.01); *C10N 2040/25* (2013.01)

(58) Field of Classification Search
CPC .............. C10M 133/54; C10M 133/14; C10M 105/00; C10M 169/04; C10M 133/12; C10M 2215/062; C10M 2215/065; C10M 2203/003; C10M 2215/26; C10M 2215/064; C10M 2216/26; C07C 217/92; C10N 2240/04; C10N 2240/08; C10N 2240/40; C10N 2240/10; C10N 2230/04; C10N 2230/10; C10N 2230/12; C10N 2030/04; C10N 2030/10; C10N 2040/04; C10N 2040/08; C10N 2040/20; C10N 2040/25

See application file for complete search history.

(56) References Cited

U.S. PATENT DOCUMENTS

| | | | |
|---|---|---|---|
| 2,369,075 A | | 2/1945 | Robbins |
| 3,751,472 A | * | 8/1973 | Wheeler .................. C08K 5/18 252/401 |
| 3,781,203 A | * | 12/1973 | Braid .................... C08G 81/021 507/221 |
| 5,338,885 A | * | 8/1994 | Immel ................... C07C 209/28 564/398 |
| 5,449,829 A | * | 9/1995 | Kusuda ................. C07C 209/26 564/307 |
| 6,599,865 B1 | | 7/2003 | Esche, Jr. et al. |
| 7,498,467 B2 | | 3/2009 | Shiraki |
| 7,501,386 B2 | | 3/2009 | Cherpeck et al. |
| 7,569,526 B2 | | 8/2009 | Costello et al. |
| 7,704,931 B2 | | 4/2010 | Dong et al. |
| 7,838,703 B2 | * | 11/2010 | Ma ........................ C07C 211/54 508/261 |
| 8,202,829 B2 | | 6/2012 | Devlin et al. |
| 2007/0082828 A1 | * | 4/2007 | Nalesnik ............... C07C 211/55 508/545 |
| 2007/0142243 A1 | | 6/2007 | Cherpeck et al. |
| 2007/0203035 A1 | | 8/2007 | Dong et al. |
| 2007/0293408 A1 | | 12/2007 | Opstal et al. |
| 2008/0318815 A1 | * | 12/2008 | Cherpeck ............. C10M 141/06 508/290 |
| 2011/0237474 A1 | | 9/2011 | Mazzamaro et al. |

FOREIGN PATENT DOCUMENTS

| | | | | |
|---|---|---|---|---|
| EP | 0165559 A1 | 12/1985 | | |
| GB | 1145189 A | 3/1969 | | |
| JP | 2011-256314 A | 12/2011 | | |
| WO | 2009067315 A1 | 5/2009 | | |
| WO | WO-2009067315 A1 | * | 5/2009 | ........... C07C 211/54 |

(Continued)

OTHER PUBLICATIONS

Poliak et al., Polymer Degradation and Stability (2015) 114, 34-44.
Zhang et al., Organic Letters, 15(8), 2018-2021, 2013, XP002775496 Abstract.
Janik et al., Physica (Amsterdam), 77(3), 514-22, 1974, XP002775497 Abstract.
Jancevska-Ni Kolovska, Rad Jugoslavenske Akademije Znanosti I Umjetnosti, 398, 93-101, 1983, XP002775498 Abstract.

(Continued)

*Primary Examiner* — Pamela H Weiss

(57) ABSTRACT

Alkylated diaryl amines further substituted by an alkoxy group on one or more aryl carbon atoms exhibit excellent antioxidant activity in lubricant compositions.

22 Claims, No Drawings

(56) References Cited

FOREIGN PATENT DOCUMENTS

WO    2012146530  A1    11/2012

OTHER PUBLICATIONS

Soulie, Tetrahedron, 57(6), 1035-1040, 2001, XP002775499 Abstract.
Zhang et al., Journal of the American Chemical Society, 134(12), 5492-5495, XP002775500 Abstract.
Kyazim-Zade et al., Neftekhimiya, 36(1), 73-75, 1996, XP002775501 Abstract.
PCT International Search Report and Written Opinion dated Nov. 24, 2017 from corresponding Application No. PCT/US2017/051334, 18 pages.
Lubricant Additives Chemistry and Applications, 2nd Ed., Leslie Rudnick, 4-43 (2009).
Lubricant Additives, Vanderbilt Worldwide Ltd. (2015).

* cited by examiner

ALKYLATED ALKOXYDIARYLAMINE ANTIOXIDANTS

Alkylated alkoxydiarylamines, such as alkylated alkoxydiphenylamines or alkylated alkoxyphenylnaphthylamines, and lubricating oil compositions comprising one or more of the alkylated alkoxydiaryl amines, which compositions exhibit excellent antioxidant and/or deposit control activity, are provided.

BACKGROUND

Lubricants are often used in demanding environments where degradation can be accelerated by high temperatures, extreme wear conditions, acidic or other corrosive conditions, etc. For example, the conditions under which automobile engines function are severe enough to require periodic oil changes to replace degraded engine lubricant in order to protect the engine against wear and damage that can lead to catastrophic failure.

Alkylated diaryl amines, such as alkylated diphenylamines (ADPAs), are well known antioxidants widely used to prevent degradation and maintain the performance of engine oils found in gasoline and diesel engines for cars and trucks, as well as a variety of industrial lubricants and lubricants for marine engines, etc. When selecting a diaryl amine antioxidant a number of performance, safety and environmental concerns must be addressed. For example, diphenylamine itself has good antioxidant activity but is known to be a sensitizer and its presence is typically kept to a minimum, e.g., less than 1% of any ADPA antioxidant. Diphenylamines substituted with hydrocarbyl groups are more soluble in lubricating oil and the higher molecular weight reduces volatility. Increased alkylation also helps to solubilize polar materials formed from oligomerization of spent oxidized amines, which reduces deposits, sludge and varnish. On the other hand, the antioxidant activity of ADPAs is dependent on the concentration of nitrogen provided and is thus inversely proportional to molecular weight and so excessive alkylation or very large alkyl groups should be avoided. NAUGALUBE 438L, a mixture of diphenylamines alkylated by one or more nonyl-chains derived from propylene trimer is an effective and widely used liquid antioxidant Diaryl amines useful as anti-oxidants bearing substituents other than alkyl groups are known but such compounds are not as common in engine oils as alkyl substituted diaryl amines.

For example, U.S. Pat. No. 7,704,931 includes 3-hydroxydiphenylamine, 4-hydroxydipenylamine and 4-isopropoxy diphenylamine in lists of possible antioxidants for lubricant compositions; U.S. Pat. No. 8,202,829 includes 3-hydroxydiphenylamine in a list of suitable antioxidants for use in a non-synthetic lubricating oil comprising less than 30 wt % monocycloparaffins and from 0.8 to 2.0 wt % tetracycloparaffins; and U.S. Pat. No. 7,569,526 includes 3-hydroxydiphenylamine and 4-hydroxydipenylamine in lists of possible antioxidants for use in the oil portion of a metal working fluid, but none of these three disclosures exemplify the use of a hydroxydiphenylamine or alkoxydiphenylamine.

U.S. Pat. No. 7,498,467 discloses aminophenol and hydroxydiphenylamine antioxidants wherein at least one phenyl ring bears a hydroxy substituent adjacent to an amino substituent.

JP 2011-256314 discloses a composition comprising an aliphatic alkylester biodiesel fuel, which fuel may also contain a fossil fuel component, and an antioxidant of the formula

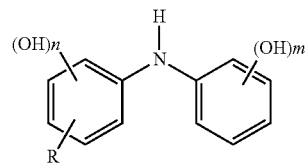

wherein n and m can be 0, 1 or 2 provided that m+n=1 or 2, and R is a C1-18 alkyl, which alkyl may be further substituted. Of the possible hydroxydiphenyl amine compounds of the above formula, only 4-hydroxydiphenylamine is exemplified.

GB 1,145,189 discloses the use of substituted 2-hydroxydiphenylamines, including 3,5-di-tert-butyl-2-hydroxy-4'ethoxy diphenylamine, as antioxidants in hydrocarbon and ester based lubricating oils.

EP 016559 discloses 3-hydroxy-4-styryldiphenylamine, which may also be further substituted by styryl at the 2- or 4'-positions, as an antioxidant for hydrocarbon and ester based lubricating oils. Compositions comprising ester based oils are exemplified.

U.S. Pat. No. 2,369,705 discloses a grease comprising alkoxy diarylamines, such as di-para-methoxydiphenylamine. No other alkoxy diarylamine is mentioned.

"Thermoanalytic study of inhibitors of oxidation of synthetic oils" Kyazim-zade, A. K.; Gadirov, A. A.; Akchurina, T. Kh., Neftekhimiya (1996), 36(1), 73-75 investigated the thermal stability and the effect on the oxidation of pentaerythritol esters at elevated temperatures of 4-hexyl-3-hydroxy-phenyl-1-naphtylamine and certain 3-hydroxyl or 3-alkoxy-4-hexyldiarylamines of the following formula:

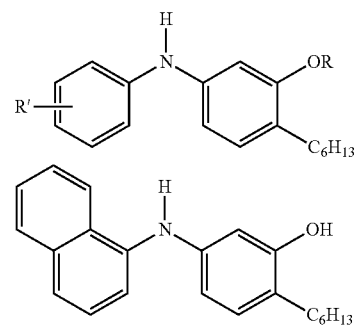

wherein R is hydrogen, butyl or hexyl and R' is hydrogen or methyl.

There is some suggestion in the literature that substitution with a hydroxyl group at the 2 and 4 positions of a diphenyl amine would lead to increased antioxidant activity, but hydroxyl substitution at the 3 position is not expected to provide the same benefit, as discussed in, for example, "Substitution and torsional effects on the energetics of homolytic N—H bond cleavage in diphenylamines" Poliak, Peter; Vaganek, Adam; Lukes, Vladimir; Klein, Erik, Polymer Degradation and Stability (2015) 114, 34-44.

Degradation of lubricating oil, e.g., oxidation of engine lubricants, can cause many undesirable effects, such as the formation of deposits, changes in viscosity and lubrictity, etc. A number of tests are commonly used in the industry to evaluate the effectiveness of antioxidants in lubricant compositions, e.g., TEOST measures deposits, PDSC is used to measure the onset of appreciable oxidation chemistry, etc. It has been found that certain diaryl amines bearing alkyl and alkoxy substituents on the aromatic rings exhibit excellent antioxidant and/or deposit control activity in lubricating oils, which activity is often superior in at least one aspect when compared to the activity of similar commercial alkylated diarylamines that are not substituted by both alkyl and alkoxy groups.

SUMMARY

The present invention provides alkylated alkoxydiarylamines of formula I or II, and lubricating oil compositions comprising them:

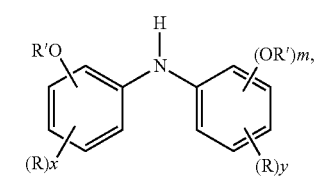

I

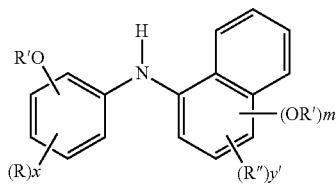

II wherein m is 0 or 1;
x is 0, 1 or 2, y is 1, 2 or 3, and y' is 0, 1, 2 or 3, provided that when x in formula II is 0 y' is 1, 2 or 3;
R' is $C_{1-12}$ alkyl, e.g., $C_{1-6}$ alkyl, or said alkyl substituted by one or more hydroxyl or alkoxy,
each R is independently $C_{4-24}$, $C_{4-18}$ or $C_{4-12}$ alkyl, $C_{7-18}$ aralkyl, or $C_{4-24}$, $C_{4-18}$ or $C_{4-12}$ alkyl substituted by one or more hydroxyl and/or interrupted by one or more oxygen atom, or two adjacent R groups together with the carbons to which they are attached form a 5 to 8 member heterocyclic ring or a 6 to 8 member non-aromatic carbocyclic ring, which heterocyclic or non-aromatic carbocyclic ring is optionally substituted by alkyl, e.g., $C_{1-4}$ alkyl, hydroxyl or alkoxy;
each R" is independently $C_{1-24}$, $C_{1-18}$ or $C_{4-12}$ alkyl, $C_{7-18}$ aralkyl, or $C_{4-24}$, $C_{4-18}$ or $C_{4-12}$ alkyl substituted by one or more hydroxyl and/or interrupted by one or more oxygen atom;
wherein at least one carbon atom adjacent to the amine nitrogen is unsubstituted, i.e., is substituted by hydrogen.

In the present disclosure, the article "a" or "an" in relation to a component means "one or more than one" unless otherwise specified.

In many embodiments of the invention, m is 0, and in many embodiments x is 0 or 1, y is 1 or 2 and y' is 1 or 2. In some embodiments the alkylated alkoxydiarylamine of the invention is a compound of formula I wherein x is 1 and y is 1, or x is 0 and y is 1, and in some embodiments the alkylated alkoxydiarylamine of the invention is a compound of formula II wherein x is 1 and y' is 1, or x is 0 and y' is 1.

DESCRIPTION

One embodiment of the invention provides a lubricating oil composition comprising
a) a lubricating oil, and
b) an alkylated alkoxydiarylamine of formula I or II.

In many embodiments, the alkoxydiarylamine antioxidant is present from about 0.1 to about 5.0 wt %, e.g., from about 0.2, 0.3, 0.4 or 0.5 to about 1.5, 2.0 or 3.0 wt %, based on the weight of the lubricating oil composition. In some embodiments, the alkoxydiarylamine antioxidant is present from about 1 or 1.5 to about 3.0 wt %. Other embodiments provide a master batch or concentrate wherein the alkoxydiarylamine antioxidant is present in greater amounts, for example from greater than 5 to 50 wt %, such as from 7 to 40 wt %, or from 10 to 35 wt %.

Diarylamines other than alkoxydiarylamines of formula I or II may also be present in the lubricant composition. As seen below, in some embodiments good results are obtained when one or more alkylated alkoxydiarylamines of formula I or II are present along with alkylated alkoxydiarylamines that are not of formula I or II, and/or simple alkylated diarylamines.

Alkylated alkoxydiarylamines of the invention are compounds of formula I or II:

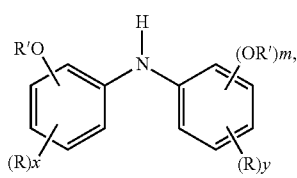

I

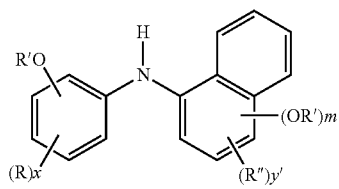

II wherein m is 0 or 1;
x is 0, 1 or 2; y is 1, 2 or 3; and y' is 0, 1, 2 or 3, provided that when x in formula II is 0 y' is 1, 2 or 3;
R' is $C_{1-12}$ alkyl, e.g., $C_{1-6}$ alkyl, or said alkyl substituted by one or more hydroxyl or alkoxy,
each R is independently $C_{4-24}$, $C_{4-18}$ or $C_{4-12}$ alkyl, $C_{7-18}$ aralkyl, or $C_{4-24}$, $C_{4-18}$ or $C_{4-12}$ alkyl substituted by one or more hydroxyl and/or interrupted by one or more oxygen atom, or two adjacent R groups together with the carbons to which they are attached form a 5 to 8 member heterocyclic ring or a 6 to 8 member non-aromatic carbocyclic ring, which heterocyclic or non-aromatic carbocyclic ring is optionally substituted by alkyl, e.g., $C_{1-4}$ alkyl, hydroxyl or alkoxy;
each R" is independently $C_{1-24}$, $C_{1-18}$ or $C_{4-12}$ alkyl, $C_{7-18}$ aralkyl, or $C_{4-24}$, $C_{4-18}$ or $C_{4-12}$ alkyl substituted by one or more hydroxyl and/or interrupted by one or more oxygen atom;
wherein at least one carbon atom adjacent to the amine nitrogen is unsubstituted, i.e., is substituted by hydrogen.

When two adjacent R groups together with the carbons to which they are attached form a 5 to 8 member heterocyclic ring, the heterocyclic ring may be aromatic or non-aromatic and typically comprises a nitrogen, oxygen or sulfur atom.

In many embodiments, each R is independently $C_{4-24}$, $C_{4-18}$ or $C_{4-12}$ alkyl (i.e. alkyl unsubstituted by hydroxyl and uninterrupted by oxygen), or two adjacent R groups together with the carbons to which they are attached form a 6 to 8 member non-aromatic carbocyclic ring, which ring is optionally substituted by $C_{1-4}$ alkyl; for example, two adjacent R groups may form a non-aromatic 6 membered ring on a compound of formula I creating a tetrahydronaphthyl ring system as in:

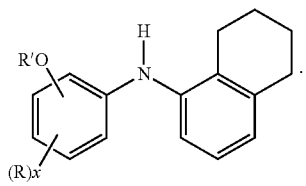

Frequently, R is $C_{4-24}$, $C_{4-18}$ or $C_{4-12}$ alkyl. Typically, R' is $C_{1-12}$ alkyl or $C_{1-6}$ alkyl. In many embodiments each R" is independently $C_{1-24}$, $C_{1-18}$ or $C_{4-12}$ alkyl.

R' as alkyl is a straight or branched chain having the specified number of carbons and includes e.g., methyl, ethyl, propyl, butyl, pentyl, hexyl, heptyl, octyl, nonyl, decyl, undecyl, dodecyl and isomers thereof, including, as non-limiting branched alkyl examples, iso-butyl, sec-butyl, tert-butyl, iso-amyl, tert-amyl, methyl hexyl, ethyl hexyl, and the like.

R as alkyl is a straight chain, branched chain, cycloalkyl or substituted cycloalkyl having the specified number of carbons and includes e.g., butyl, pentyl, hexyl, heptyl, octyl, nonyl, decyl, undecyl, dodecyl, tetradecyl, hexadecyl, octadecyl, icosane, docosane, tetracosane etc., and isomers thereof, including, as non-limiting branched alkyl examples, iso-butyl, sec-butyl, tert-butyl, iso-amyl, tert-amyl, methyl hexyl, ethyl hexyl, t-octyl, methyloctyl, ethylheptyl, propylhexyl, dimethylbutyl, dimethyheptyl, trimethylhexyl, tetramethylpentyl, ethylmethylhexyl, ethyl dimethyl pentyl, diethyl pentyl, isopropylhexyl, and the like.

R" as alkyl is the same as R as alkyl except that in some embodiments R" can also be methyl, ethyl, propyl or iso-propyl.

In the present application, "alkyl" in general relates to straight chain, branched chain, or cyclic alkyl. Unless otherwise specified, terms such as "octyl" or "nonyl" and the like relate to a straight or branched chain alkyl. The above descriptions incorporate the term "and isomers thereof" as a formal acknowledgement of this and in order to avoid confusion. It is noted that many reactions used to alkylate an aromatic ring make use of oligomers formed from smaller olefins, such as propylene trimers, tetramers or pentamers, and the alkyl substituents formed therefrom are referred to herein as nonyl, dodecyl and pentadecyl.

R or R" as $C_{7-18}$ aralkyl is a straight or branched chain alkyl substituted by phenyl or naphthyl, which phenyl or naphthyl may be further substituted by alky, wherein the total number of carbon atoms is from 7 to 18 and includes, e.g., benzyl, 1 or 2-phenethyl, cumyl, 1, 2 or 3-phenyl propyl, butylphenethyl, and the like.

R or R" as alkyl interrupted by one or more oxygen atom is an ether or polyether of the specified number of carbons, wherein the alkyl segments may be straight chain, branched chain, cycloalkyl or substituted cycloalkyl, e.g., ethoxyethyl, propoxypropyl, butoxybutyl, hexyloxyhexyl, tert-butoxypropyl, tert-butoxybutyl, 2-ethylhexyloxyethyl and the like, a polyalkylene ether presented by the general formula R'O(R'O)$_n$R", wherein each R' is independently $C_{2-6}$ alkylene, R" is $C_{2-6}$ alkyl, and n is a number of from 1 to 12, provided that the total number of carbons is from 4 to 24, 4 to 18, or 4 to 12.

In many embodiments of the invention, m is 0, as in, e.g., a compound of formula III or IV,

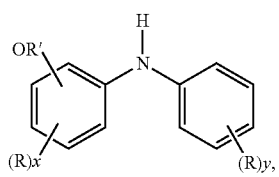

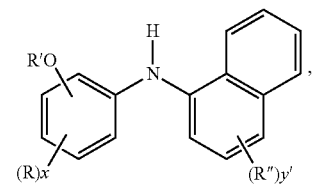

wherein R, R', R", x, y and y' are as defined above.

In many embodiments of the invention, x is 0 or 1 and y is 1 or 2. For example in some embodiments, the alkylated alkoxydiarylamine of the invention is a compound of formula I wherein x is 1 and y is 1, or x is 0 and y is 1; for example, a compound of formula IIIa or IIIb:

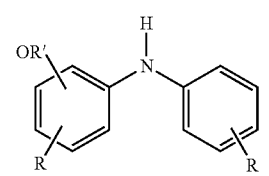

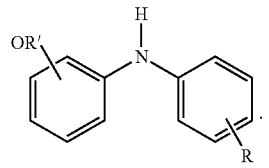

In some embodiments of the invention, x is 0 or 1 and y' is 1 or 2. For example in some embodiments, the alkylated alkoxydiarylamine of the invention is a compound of formula II or formula IV wherein x is 1 and y' is 1 or x is 0 and y' is 1; for example, a compound of formula IVa or IVb:

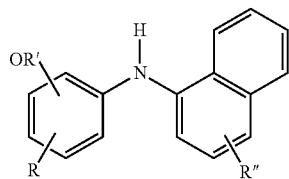

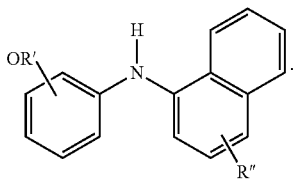

IVb

The alkylated alkoxydiarylamines of the invention may be substituted by alkoxy on any aryl ring carbon atom. In some embodiments, the alkylated alkoxydiarylamines of the invention are compounds of formula I or II substituted by alkoxy on a phenyl ring at the 2- or 3-position relative to the nitrogen atom. For example, in some particular embodiments, the alkylated alkoxydiarylamines of the invention bear a single alkoxy group on a phenyl ring at the 2- or 3-position relative to the nitrogen atom, and in certain embodiments, the alkylated alkoxydiarylamines of the invention bear a single alkoxy group on a phenyl ring at the 3-position relative to the nitrogen, as in formula V or VI:

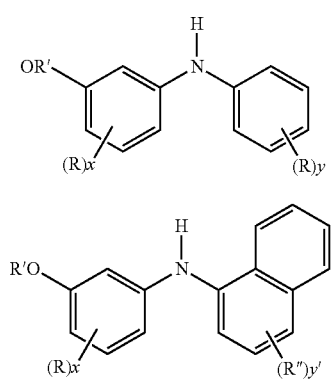

wherein R', R, R", x, y and y' are as defined above.

Typically, alkylated alkoxydiarylamines of the invention are compounds of formula I or II, where the total number of carbon atoms of the groups R', R and R" combined is 8, 9, 10 or higher.

In select embodiments of the invention, the total number of carbon atoms of the combined groups R', R and R" is at least 12, e.g., 16, 18 or higher, and in certain embodiments, the total number of carbon atoms of the combined groups R', R and R" is 20 or higher. In some select embodiments, the total number of carbon atoms of the combined groups R and R" is at least 12, e.g., 16, 18, 20 or higher. Generally, in such select embodiments, R, R' and R" are not substituted by hydroxyl or interrupted by oxygen atoms. Frequently in these select embodiments, but not always, both aryl groups will be alkylated. Examples include, but are not restricted to, compounds of formula V wherein:

x is 0, y is 1, R' is methyl or ethyl, and R is dodecyl, octadecyl, or icosane;

x is 1, y is 1, R' is methyl or ethyl, and R is selected from hexyl, octyl, nonyl, decyl, and dodecyl;

x is 1, y is 1, R' is methyl or ethyl, one R is n-butyl, sec-butyl, tert-butyl or hexyl and the other R is t-octyl, nonyl, dodecyl, hexadecyl or octadecyl;

x is 1, y is 1, R' is butyl or hexyl, and R is selected from n-butyl, sec-butyl, iso-amyl, hexyl, octyl, nonyl, or dodecyl.

Many commercial diarylamine antioxidants comprise mixtures of compounds, e.g., mixtures of mono- and di-alkylated dipenylamines, positional isomers formed by alkylation at different ring carbons, compounds with homologous alkyl substituents due to the ready availability of alkylating agents comprising homologues, different levels of branching, different positions of the double bond etc. The commercial mixtures of diaryl amines are often the result of synthetic methods, or the use of less expensive stating materials comprising mixtures, but there are often advantages in using a mixture of compounds, e.g., mixtures are more likely to be liquids.

Individual compounds of formula I and II are described, however methods for preparing such compounds may provide mixtures comprising one or more compounds of formula I or II. For example, the process of Example 2 provides mainly a single compound of formula I, while the process of Example 3 provides a mixture of mono-substituted isomers comprising the compound of Example 2.

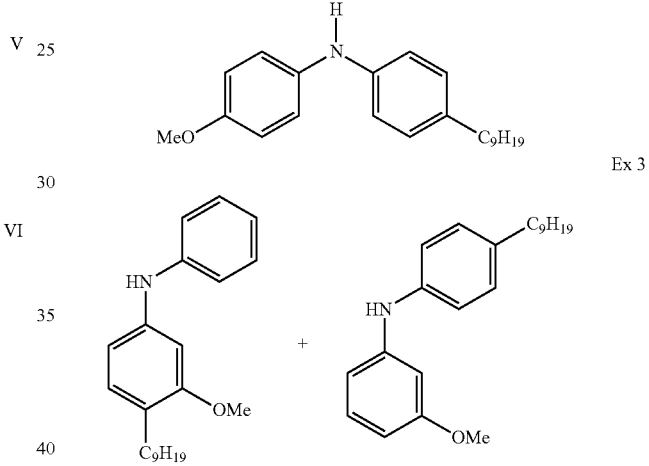

Thus, individual alkylated alkoxydiaryl amines of the invention. i.e., compounds of formula I or II, mixtures comprising more than one alkylated alkoxydiaryl amines of the invention, and mixtures comprising one or more alkylated alkoxydiaryl amines of formula I or II plus amine alkoxydiaryl antioxidants not of formula I or II, can be prepared directly by selection of starting materials and reaction conditions.

Other additives as known in the art may be present in the present lubricating oil composition. For example, commercial lubricant formulations typically contain a variety of other additives, for example, dispersants, detergents, corrosion/rust inhibitors, other antioxidants including amine, phenol or phosphorus antioxidants, anti-wear agents, anti-foamants, friction modifiers, seal swell agents, demulsifiers, V.I. improvers, pour point depressants, and the like. A sampling of these additives can be found in, for example, U.S. Pat. Nos. 5,498,809 and 7,696,136, the relevant portions of each disclosure is incorporated herein by reference, although the practitioner is well aware that this comprises only a partial list of available lubricant additives. It is also well known that one additive may be capable of providing or improving more than one property, e.g., an anti-wear agent may also function as a friction modifier and/or an extreme pressure additive.

For example, in addition to the alkylated alkoxydiarylamine of the invention, other diarylamines may be present in the lubricant compositions, such as alkyldiarylamines, hydroxydiarylamines, other alkoxydiarylamines, and the like, for example, the lubricating oil composition of the invention may also contain one or more alkylated diphenylamines, many of which are commercially available.

Certain embodiments of the invention relate to compositions comprising a mixture of an alkylated alkoxydiarylamine of the invention and one or more other antioxidants. Of particular interest are embodiments wherein the mixture of an alkylated alkoxydiarylamine with an antioxidant such as an amine antioxidant, nitrogen containing heterocyclic antioxidant, phenol antioxidant, phosphorus containing antioxidant and/or another known antioxidant provides better stabilization performance in a lubricant than either antioxidant used on its own.

The following table shows the results of standard TEOST deposit formation testing and standard PDSC oxidation onset testing of lubricating oil compositions comprising a commercial grade hydrocarbon engine oil and 2 wt % of a selection of alkoxydiarylamine antioxidants of the invention compared to the results obtained using 2 wt % of the commercial diphenylamine NAUGALUBE 438L. The TEOST data is in mg of deposits, a lower value means less deposits, and the PDSC data is in minutes until onset of oxidation, a higher value represents greater protection. Additional data can be found in the Examples.

| Example | PDSC | TEOST |
|---------|------|-------|
| 438L | 16.2 | 44.1 |
| 2 | 26 | 31.8 |
| 3 | 24.7 | 33.7 |
| 5 | 22.7 | 41.2 |
| 7 | 17.1 | 42.2 |
| 12 | 17.4 | 27.3 |

Ex 2

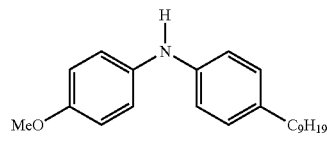

Ex 3

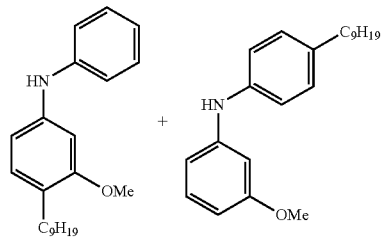

Ex 5

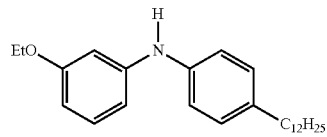

Ex 7

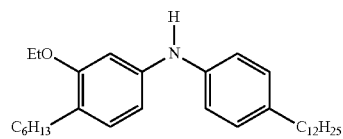

Ex 12

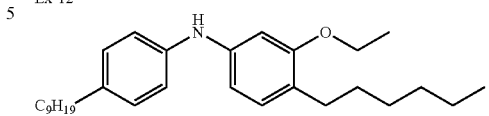

During testing, it was discovered that many of the alkoxydiarylamine antioxidants of the invention showed a greater performance variance with load level than the commercial standard NL 438L. The following table lists data obtained at concentrations of 1, 2 and 3 wt % of alkoxydiarylamine antioxidants vs the standard NL 438L.

| | TEOST | | | PDSC | | |
|---|---|---|---|---|---|---|
| | 1 wt % | 2 wt % | 3 wt % | 1 wt % | 2 wt % | 3 wt % |
| NL438L | >60 | 44.1 | 20.7 | 11.1 | 16.2 | 26.7 |
| Ex 3 | >60 | 34 | 7 | 14.2 | 24.7 | 38.1 |
| Ex 5 | >60 | 41.2 | 13.3 | 14.6 | 22.7 | 41 |
| Ex 7 | >60 | 42.2 | 9.3 | 10.6 | 17.1 | 27.5 |
| Ex 12 | ~60 | 27.3 | — | 9.8 | 17.4 | — |

In one particular embodiment, the lubricating oil comprises one or more hydrocarbon base stocks, however, in other embodiments other types of base stocks and mixtures of various types of base stocks are used.

The lubricating oil of the invention can be any suitable oil of lubricating viscosity as described for example, in co-pending U.S. application Ser. No. 12/371,872, the relevant portions of which are incorporated herein by reference. For example, a lubricating oil base stock is any lubricating oil base stock, or mixtures thereof, having a kinematic viscosity at 100° C. of about 2 to about 200 cSt, about 3 to about 150 cSt, and often about 3 to about 100 cSt. Suitable lubricating oil base stocks include, for example, mineral oils such as those derived from petroleum, oils derived from coal or shale, animal oils, vegetable oils and synthetic oils. The relevant portions of co-pending U.S. application Ser. No. 12/371,872 are incorporated herein by reference.

Synthetic oils include hydrocarbon oils and halo-substituted hydrocarbon oils, such as polymerized and interpolymerized olefins, gas-to-liquids prepared by Fischer-Tropsch technology, alkylbenzenes, polyphenyls, alkylated diphenyl ethers, alkylated diphenyl sulfides, as well as their derivatives, analogs, homologs, and the like. Synthetic lubricating oils also include alkylene oxide polymers, interpolymers, copolymers, and derivatives thereof, wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from monocarboxylic acids or diacids and polyols and polyol ethers. Other esters useful as synthetic oils include those made from copolymers of alphaolefins and dicarboxylic acids which are esterified with short or medium chain length alcohols.

The synthetic oils may comprise at least one of an oligomer of an α-olefin, an ester, an oil derived from a Fischer-Tropsch process, and a gas-to-liquid stock. Synthetic base stock lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1 octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and derivative, analogs, and homologs thereof.

Silicon-based oils, such as the polyalkyl-, polyaryl-, polyalkoxy-, or polyaryloxy-siloxane oils and silicate oils, comprise another useful class of synthetic lubricating oils. Other synthetic lubricating oils include liquid esters of phosphorus-containing acids, polymeric tetrahydrofurans, poly alphaolefins, and the like.

Lubricating oil base stocks derived from the hydroisomerization of wax may also be used, either alone or in combination with the aforesaid base stocks. Such wax isomerate oil is produced by the hydroisomerization of waxes or mixtures thereof over a hydroisomerization catalyst. Natural waxes are typically the slack waxes recovered by the solvent dewaxing of mineral oils; synthetic waxes are typically the waxes produced by the Fischer-Tropsch process.

In many embodiments, the oil base stock comprises mineral oils. For example, the lubricating oil of the invention may be a petroleum oil, or a mixture comprising a petroleum oil. Many other embodiments include vegetable oils, paraffinic oils, naphthenic oils, aromatic oils, and derivatives thereof, often as combination of base stocks.

Useful base stocks from vegetable and animal sources include, for example, alkyl esters of fatty acids, which include commercial mixtures of the ethyl, propyl, butyl and especially methyl esters of fatty acids with 12 to 22 carbon atoms. For example, lauric acid, myristic acid, palmitic acid, palmitoleic acid, stearic acid, oleic acid, elaidic acid, petroselic acid, ricinoleic acid, elaeostearic acid, linoleic acid, linolenic acid, eicosanoic acid, gadoleic acid, docosanoic acid, or erucic acid are useful and have an iodine number from 50 to 150, especially 90 to 125. Mixtures with particularly advantageous properties are those which contain mainly, i.e., at least 50 wt. %, methyl esters of fatty acids with 16 to 22 carbon atoms and 1, 2, or 3 double bonds. The preferred lower alkyl esters of fatty acids are the methyl esters of oleic acid, linoleic acid, linolenic acid, and erucic acid.

Often the base stock of lubricating viscosity can comprise a Group I, Group II, or Group III base stock or base oil blends of the aforementioned base stocks, for example, the oil of lubricating viscosity is a Group II or Group III base stock, or a mixture thereof, or a mixture of a Group I base stock and one or more of a Group II and Group III. Generally, a major amount of the oil of lubricating viscosity is a Group II, Group III, Group IV, or Group V base stock, or a mixture thereof. The base stock, or base stock blend, typically has a saturate content of at least 65%, e.g., at least 75% or at least 85%. Most preferably, the base stock, or base stock blend, has a saturate content of greater than 90%.

Definitions for the base stocks and base oils in this invention are the same as those found in the American Petroleum Institute (API) publication "Engine Oil Licensing and Certification System," Industry Services Department (14th ed., December 1996), Addendum 1, December 1998. This publication categorizes base stocks as follows.

(a) Group I base stocks contain less than 90 percent saturates (as determined by ASTM D 2007) and/or greater than 0.03 percent sulfur (as determined by ASTM D 2622, ASTM D 4294, ASTM D 4927 and ASTM D 3120) and have a viscosity index greater than or equal to 80 and less than 120 (as determined by ASTM D 2270).

(b) Group II base stocks contain greater than or equal to 90 percent saturates (as determined by ASTM D 2007) and less than or equal to 0.03 percent sulfur (as determined by ASTM D 2622, ASTM D 4294, ASTM D 4927 and ASTM D 3120) and have a viscosity index greater than or equal to 80 and less than 120 (as determined by ASTM D 2270).

(c) Group III base stocks contain greater than or equal to 90 percent saturates (as determined by ASTM D 2007) and less than or equal to 0.03 percent sulfur (as determined by ASTM D 2622, ASTM D 4294, ASTM D 4927 and ASTM D 3120) and have a viscosity index greater than or equal to 120 (as determined by ASTM D 2270).

(d) Group IV base stocks are polyalphaolefins (PAO).

(e) Group V base stocks include all other base stocks not included in Groups I-II, III, or IV.

The lubricating oil compositions of the invention can be used in a variety of applications, for example, crankcase lubricating oils for spark-ignited and compression-ignited internal combustion engines, gas engine lubricants, wind turbine lubricants, automatic transmission fluids, gear lubricants, compressor lubricants, metal-working lubricants, hydraulic fluids, and other lubricating oil and grease compositions.

EXAMPLES

Non-commercially available hydroxydiaryl amines used as starting materials in the following examples were prepared by reacting the appropriately substituted aniline with an appropriately substituted 1,2-, 1,3-, or 1,4-dihydroxybenzene derivative at elevated temperatures in the presence of triphenyl phosphine, p-toluene sulfonic acid or basic alumina. Specific procedures can be found in copending applications entitled "Lubricant Compositions Stabilized by Mixtures of Diarylamine and Hydroxydiarylamine Antioxidants" and "Alkylated 3-Hydroxydiarylamine Antioxidants" filed on the same day as the present application.

Example 1, General Procedure

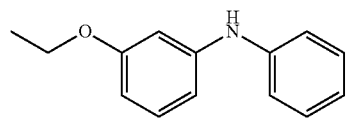 [SMILES: CCOc1cccc(Nc2ccccc2)c1]

A 250 mL 24/40 three-neck flask with thermocouple adapter equipped with a magnetic stir bar, spiral condenser, nitrogen inlet, thermocouple, and two stoppers was charged with 29.8 g 3-hydroxydiphenylamine, 100 mL xylenes, 1.0 g tetrabutylammonium bromide, and 8.9 g sodium hydroxide in 55 mL water. The mixture was warmed with stirring to 83° C. Ethyl bromide (20.9 g) was added, and the reaction was stirred for 7 h. The aqueous layer was removed and the reaction was washed three times with water. Volatiles were removed by distillation at atmospheric pressure, followed by rotary evaporation of the residual. The crude reaction mass (32.9 g) was recrystallized from a hexanes/isopropanol, and then recrystallized again from hexanes/ethyl acetate to yield 14.5 light brown g crystals, mp 57-58° C.

Example 2

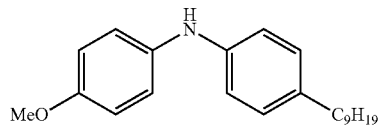

A 100 mL three-neck flask equipped with an overhead stirrer, Claisen head with a thermocouple and an addition funnel, and a spiral condenser was charged with 27.2 g 4-methoxydiphenylamine, 6.0 g Filtrol 20× (oven dried 3 h at 150° C.) and 17.2 g propylene trimer. The reaction was heated to 140° C. for 1 h. An additional 34.6 g propylene trimer was added slowly over 8 h, and the reaction was stirred for 5.5 h. The reaction mass was filtered through diatomaceous earth. Volatiles were removed by rotary evaporation followed by vacuum distillation to yield 32.4 g light red waxy solid.

Example 3

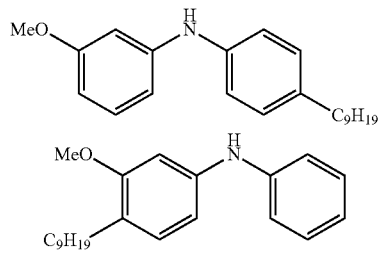

Using a procedure similar to Example 2, 30.2 g 3-methoxydiphenylamine (TCl), 6.0 g Filtrol 20× (oven dried 3 h at 150° C.) and 21.1 g propylene trimer was stirred in a 250 mL three neck flask at 140° C. for 1.5 h. An additional 41.8 g propylene trimer was added slowly over 12 h, and the reaction was stirred for 1 h. The reaction mass was filtered through diatomaceous earth. Volatiles were removed by vacuum distillation to yield 27.7 g clear red oil.

Example 4

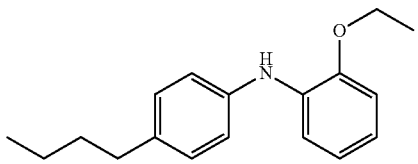 [SMILES: CCCCc1ccc(Nc2ccccc2OCC)cc1]

Using a procedure similar to Example 1, 4.8 g 4-butyl-2'-hydroxydiphenylamine, 23 mL xylenes, 0.8 g tetrabutylammonium bromide, and 3.3 g ethyl bromide were warmed, and a solution of 1.6 g sodium hydroxide in 9.6 mL water was added. The reaction was stirred at 82° C. for 5.5 h. An additional 0.5 g ethyl bromide was added, and the reaction was stirred for 3 h. The aqueous layer was removed and the reaction was washed four times with water. Volatiles were removed by distillation at atmospheric pressure, and the product was collected by vacuum distillation.

Example 5

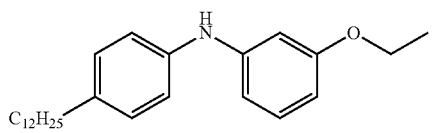

A 250 mL three-neck flask with equipped with an overhead stirrer, spiral condenser with nitrogen inlet, and a thermocouple was charged with 27.6 g 4-dodecyl-3'-hydroxy-diphenylamine, 100 mL xylenes, 1.9 g tetrabutylammonium bromide, and 12.8 g ethyl bromide. The mixture was warmed with stirring to 82° C. A solution of 0.8 sodium hydroxide in 7.4 mL water was added was added, and the reaction was stirred at 88° C. for 3.3 h. The aqueous layer was removed and the reaction was washed four times with water. Volatiles were removed by distillation at atmospheric pressure, followed by rotary evaporation of the residual to yield 29.5 g clear dark yellow brown liquid.

Example 6

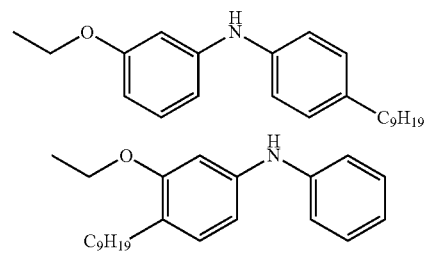

A 50 mL three-neck flask with equipped with a magnetic stir bar, spiral condenser with nitrogen inlet, thermocouple, and a stopper was charged with 4.7 g nonylated-3-hydroxy-diphenylamines, 22 mL xylenes, 0.6 g tetrabutylammonium bromide, and 2.4 g ethyl bromide. The mixture was warmed with stirring to 78° C. A solution of 1.1 sodium hydroxide in 9.8 mL water was added, and the reaction was stirred at 81° C. for 80 min. The aqueous layer was removed and the reaction was washed three times with water. Volatiles were removed by distillation at atmospheric pressure, followed by rotary evaporation of the residual to yield 5.8 g clear dark red viscous liquid.

Example 7

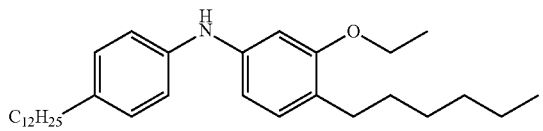

A 50 mL three-neck flask with equipped with a magnetic stir bar, spiral condenser with nitrogen inlet, thermocouple, and a stopper was charged with 4.4 g 4-dodecyl-4'-hexyl-3'-hydroxydiphenylamines 22 mL xylenes, 0.6 g tetrabutylammonium bromide, and 1.7 g ethyl bromide. The mixture was warmed with stirring to 74° C. A solution of 0.8 g sodium hydroxide in 7.4 g water was added, and the reaction was stirred at 79° C. for 110 min. The aqueous layer was removed and the reaction was washed three times with water. Volatiles were removed by distillation at atmospheric pressure, followed by rotary evaporation of the residual to yield 4.6 g clear dark red viscous liquid.

Example 8

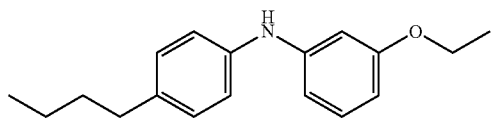 [SMILES: CCCCc1ccc(Nc2cccc(OCC)c2)cc1]

Following the procedure of Example 4, a mixture of 4-butyl-3'-hydroxydiphenylamine, xylenes, tetrabutylammonium bromide, and ethyl bromide was warmed, and a solution of sodium hydroxide in water was added. The reaction was stirred at 82° C. for 5.5 h. An additional portion of ethyl bromide was added, and the reaction was stirred for 3 h. The aqueous layer was removed and the reaction was washed four times with water. Volatiles were removed by distillation at atmospheric pressure, and the product was collected by vacuum distillation.

Example 9

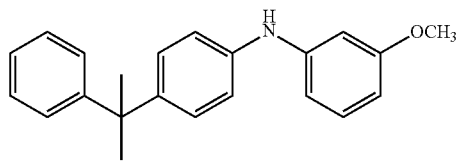

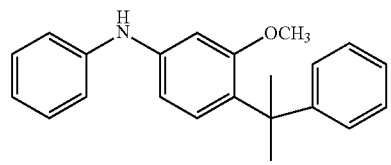

A 100 mL three neck flask, equipped with a Claisen head with a thermocouple and nitrogen inlet, an overhead stirrer, and a short path distillation apparatus was charged with 10.7 g 3-methoxydiphenylamine, 15.0 mL n-octane, and 1 g aluminum chloride. The mixture was heated to 120° C., and α-methyl styrene, 6.6 g, was added over 60 min. The reaction was stirred at 120° C. for an additional 60 min. The reaction mixture was taken up in xylenes/ethyl acetate/isopropanol, and extracted with aqueous ammonium hydroxide, then washed three times with water. Volatiles were removed by rotary evaporation followed by vacuum distillation, to yield 13.3 g clear orange viscous liquid.

Example 10 (Comparative)

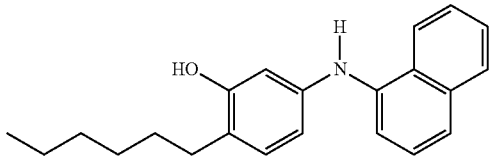 [SMILES: CCCCCCc1ccc(Nc2cccc3ccccc23)cc1O]

A mixture of 21.2 g 3-hexylresorcinol, 9.2 g 1-naphthylamine, and 14.4 g basic alumina was stirred at 200-220° C. for 39 h using to yield the product as yellow brown crystals.

Example 11

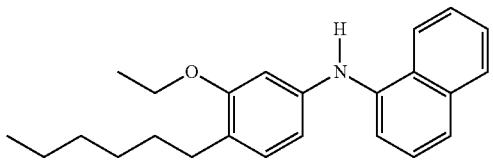 [SMILES: CCCCCCc1ccc(Nc2cccc3ccccc23)cc1OCC]

A 50 mL three-neck flask with equipped with a magnetic stir bar, spiral condenser with nitrogen inlet, thermocouple, and a stopper was charged with 5.0 g 4-hexyl-3-hydroxyphenyl-1-naphtylamine, 22 mL xylenes, 0.6 g tetrabutylammonium bromide, and 2.7 g ethyl bromide. The mixture was warmed with stirring. A solution of 1.4 g sodium hydroxide in 8.9 mL water was added and the reaction was stirred at 82° C. for 5.5 h. The aqueous layer was removed and the reaction was washed four times with water. Volatiles were removed by distillation at atmospheric pressure, followed by rotary evaporation of the residual to yield 5.3 g clear orange brown liquid.

Example 12

A 250 mL three-neck flask, equipped with an overhead stirrer, thermocouple, and a spiral condenser with nitrogen inlet was charged with 20 g 4-nonyl-4'-hexyl-3'-hydroxydiphenylamine, 60 mL xylenes, and 39.9 g 10% sodium hydroxide. The reaction was heated to 86° C., and 1.2 g tetrabutylammonium bromide was added, followed by 8.2 g ethyl bromide. The reaction was stirred for 2.3 h, then the aqueous phase was removed, and the reaction was washed with four 65 mL portions of water. Volatiles were removed by distillation at atmospheric pressure, followed by rotary evaporation of the residual to yield 20.3 g clear orange liquid

Example 13

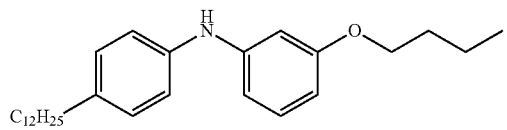

A 100 mL 14/20 three-neck flask with thermocouple adapter equipped with an overhead stirrer, spiral condenser, nitrogen inlet, thermocouple, and was charged with 14.16 g 4-dodecyl-3'-hydroxy-diphenylamine, 3.26 g sodium hydroxide in 16 mL water, and 0.299 g tetrabutylammonium bromide. The mixture was warmed with stirring to 45° C. Butyl bromide (5.502 g) was added, and the reaction was heated to 84° C. and stirred for 3.5 h. An additional 0.152 g butyl bromide was added, and reaction was stirred for an additional 5 h. The organic layer was taken up in xylenes and ethyl acetate, and the reaction was washed four times with water. Volatiles were removed by rotary evaporation of the residual to yield 16.27 viscous brown liquid.

Example 14

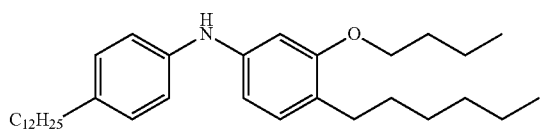

A 100 mL 14/20 three-neck flask with thermocouple adapter equipped with an overhead stirrer, spiral condenser, nitrogen inlet, thermocouple, and was charged with 15.45 g 4-dodecyl-4'-hexyl-3'-hydroxy-diphenylamines, 2.90 g sodium hydroxide in 14 mL water, and 0.269 g tetrabutylammonium bromide. The mixture was warmed with stirring to 45° C. The reaction was heated to 80° C., and butyl bromide (4.94 g) was added. The reaction was stirred for 3.7 h. An additional 0.518 g butyl bromide was added, and reaction was stirred for an additional 2.5 h. The reaction was taken up in xylenes, and the aqueous layer was removed. The reaction was washed four times with water. Volatiles were removed by rotary evaporation of the residual, followed by removal of a minor portion by distillation at 0.6 torr to yield 16.27 orange liquid. PDSC and TEOST testing of compositions comprising a commercial grade hydrocarbon motor oil and 2 wt % of compounds from the above examples compared to a similar composition comprising NAUGALUBE 438 L.

| | 2 wt % Additive | |
|---|---|---|
| Example | PDSC | TEOST |
| NL 438L | 16.2 | 44.1 |
| 2 | 26 | 31.8 |
| 3 | 24.7 | 33.7 |
| 4 | 32.5 | 21.2 |
| 5 | 22.7 | 41.2 |
| 6 | 25.2 | 35.6 |
| 7 | 17 | 42.2 |
| 8 | 39.4 | 29.7 |
| 9 | 23.2 | 35.4 |
| 10 (comp) | 15 | 55 |
| 11 | 18 | 24 |
| 12 | 17.4 | 27.3 |

Alkylated alkoxydiarylamines of the invention were also tested at other concentrations, in combination with other antioxidants, and using alternate methods, i.e., RPVOT.

| | 1% | | 1.5% | | 2% | | 2.5% | 3% |
|---|---|---|---|---|---|---|---|---|
| | PDSC | TEOST | PDSC | TEOST | PDSC | TEOST | PDSC | PDSC |
| N438L | 11.1 | 72.8 | 14.5 | 56.6 | 16.2 | 44.1 | 18.6 | 22.8 |
| Ex 2, 3 | 14.2 | | 19.8 | | 24.7 | | 31.1 | 38.1 |
| Ex 5 | 14.6 | 67.5 | 17.7 | 52.7 | 22.7 | 41.2 | | ~41 |
| Ex 7 | 10.6 | 68 | 14.5 | 50.8 | ~16 | 42.2 | | ~28 |
| Ex 12 | | 60.4 | | 46.6 | | 27.3 | | |
| Ex 13 | | | | 55.1 | | | | 27.8 |
| Ex 14 | | | | 45.1 | | | | 21.2 |

| Oxidation induction time by RPVOT: | | |
|---|---|---|
| | 0.5% Single Additive | 0.25% NL 438NL/ 0.25% Example |
| N438L | 280 | |
| Ex 2, 3 | 1440 | 1036 |
| Ex 5 | ~1600 | 1130 |
| Ex 7 | 1240 | 828 |
| EX 12 | 1221 | 943 |
| Ex 13 | 1472 | 849 |
| Ex 14 | 1101 | 773 |

| | 3 wt % Additive | | | | | | |
|---|---|---|---|---|---|---|---|
| | Single Additive | | *Mixture w/ 50% NL 438L | | Mixture w/ 50% NL APAN | | Mix w/ 50% NL 531 |
| | TEOST | PDSC | TEOST | PDSC | TEOST | PDSC | TEOST |
| NL 438L | 20.7 | 26.7 | — | — | — | — | — |
| NL APAN | 16.3 | 22.1 | — | — | — | — | — |
| NL 531 | 50.3 | — | — | — | — | — | — |
| Ex 5 | 13.3 | 41 | 23 | 33.2 | 17.7 | 37 | 17.2 |
| Ex 7 | 9.3 | 27.5 | 10.4 | 33.5 | 16.6 | 25.5 | 6.6 |
| Ex 13 | 22.6 | 27.8 | 21.7 | 23.7 | | | |
| Ex 14 | 13.6 | 21.2 | 14.5 | 22.1 | | | |

*1.5% N-438L plus about 1.5% of the experimental, with the exact charge of experimental adjusted to have a Nitrogen content equal to 3% N-438L.

What is claimed:

1. A lubricating oil composition comprising
a) a lubricating oil, and
b) one or more alkylated alkoxydiarylamine of formula III:

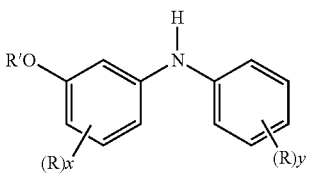

wherein x is 0, 1 or 2 and y is 1, 2 or 3;
R' is $C_{1-12}$ alkyl or $C_{1-12}$ alkyl substituted by one or more hydroxyl or alkoxy;
each R is independently $C_{4-24}$ alkyl, $C_{7-18}$ aralkyl, or $C_{4-24}$ alkyl substituted by one or more hydroxyl and/or interrupted by one or more oxygen atom;
wherein the total number of carbon atoms of the combined groups R is 12 or higher, and wherein at least one carbon atom adjacent to the amine nitrogen is unsubstituted.

2. The lubricating oil composition according to claim 1 wherein b) is present in an amount of about 0.1 to about 5.0 wt%, based on the weight of the lubricating oil composition.

3. The lubricating oil composition according to claim 1 wherein b) is present in an amount of greater than 5 wt%, up to about 50 wt%, based on the weight of the lubricating oil composition.

4. The lubricating oil composition according to claim 1 further comprising one or more alkylated diarylamine not substituted by an alkoxy group.

5. The lubricating oil composition according to claim 1 wherein in the alkylated alkoxydiarylamine of the formula III x is 0 or 1 and y is 1.

6. The lubricating oil composition according to claim 1 wherein the alkoxy group of the alkoxydiarylamine is at the 3-position relative to the nitrogen according to formula V:

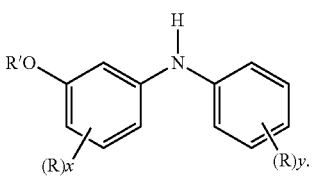

7. The lubricating oil composition according to claim 1 wherein the total number of carbon atoms of the combined groups R is 16 or higher.

8. The lubricating oil composition according to claim 6 wherein in the alkylated alkoxydiarylamine of the formula V x is 0 or 1 and y is 1.

9. The lubricating oil composition according to claim 6 wherein in the alkylated alkoxydiarylamine of the formula V x is 1 and y is 1.

10. The lubricating oil composition according to claim 1, wherein the alkoxy group R'O is on the phenyl ring at the 2- or 3-position relative to the nitrogen atom.

11. The lubricating oil composition according to claim 1, wherein x is 1 and y is 1.

12. The lubricating oil composition according to claim 1, wherein both aryl groups in the formula III are alkylated.

13. The lubricating oil composition according to claim 1 wherein x is 0, y is 1, R' is methyl or ethyl, and R is selected from dodecyl, octadecyl, and icosane.

14. The lubricating oil composition according to claim 1 wherein x is 1, y is 1, R' is methyl or ethyl, and R is selected from hexyl, octyl, nonyl, decyl, and dodecyl.

15. The lubricating oil composition according to claim 1 wherein x is 1, y is 1, R' is methyl or ethyl, and one R is n-butyl, sec-butyl, tert-butyl or hexyl and the other R is t-octyl, nonyl, dodecyl, hexadecyl or octadecyl.

16. The lubricating oil composition according to claim 1 wherein x is 1, y is 1, R' is butyl or hexyl, and R is selected from n-butyl, sec-butyl, iso-amyl, hexyl, octyl, nonyl, and dodecyl.

17. The lubricating oil composition according to claim 1, wherein the lubricating oil comprises one or more hydrocarbon base stocks.

18. The lubricating oil composition according to claim 1 wherein x is 0 or 1 and y is 1 or 2.

19. The lubricating oil composition according to claim 1 wherein R' is $C_{1-12}$ alkyl.

20. The lubricating oil composition according to claim 1 wherein each R is independently $C_{4-24}$ alkyl.

21. The lubricating oil composition according to claim 20 wherein R' is $C_{1-6}$.

22. The lubricating oil composition according to claim 21 wherein x is 0 or 1 and y is 1 or 2.

* * * * *